（12）United States Patent
Boehm et al.

(10) Patent No.: US 10,416,054 B2
(45) Date of Patent: Sep. 17, 2019

(54) BLOOD COLLECTOR WITH CAPILLARY STRUCTURE

(71) Applicant: Roche Diagnostics Operations, Inc., Indianapolis, IN (US)

(72) Inventors: Christoph Boehm, Viernheim (DE); Thorsten Brueckner, Schriesheim (DE); Sascha Lutz, Neustadt (DE); Bruntje Esrom, Ladenberg (DE); Michael Herbel, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 175 days.

(21) Appl. No.: 15/387,007

(22) Filed: Dec. 21, 2016

(65) Prior Publication Data

US 2017/0176306 A1    Jun. 22, 2017

(30) Foreign Application Priority Data

Dec. 21, 2015   (EP) ..................................... 15201585

(51) Int. Cl.
*G01N 1/40*       (2006.01)
*G01N 1/10*       (2006.01)
(Continued)

(52) U.S. Cl.
CPC .......... *G01N 1/4077* (2013.01); *A61B 5/1411* (2013.01); *A61B 5/157* (2013.01);
(Continued)

(58) Field of Classification Search
CPC .............. A61B 10/0045; A61B 5/1411; A61B 5/150022; A61B 5/150213;
(Continued)

(56) References Cited

U.S. PATENT DOCUMENTS 8,114,351 B2    2/2012  Degenhardt
2003/0039587 A1*  2/2003  Niermann ........ A61B 5/150022
422/400

(Continued)

FOREIGN PATENT DOCUMENTS

EP    1285628 A2    2/2003
EP    2777499 A1    9/2014
(Continued)

OTHER PUBLICATIONS

European Search Report dated Jun. 21, 2016 in reference to co-pending European Patent Application No. EP15201585.5 filed Dec. 21, 2015.

(Continued)

*Primary Examiner* — Maureen Wallenhorst
(74) *Attorney, Agent, or Firm* — Dinsmore & Shohl, LLP

(57) ABSTRACT

System and method of determining an amount of an analyte in a blood sample using a cartridge and blood collector are disclosed. The blood collector has a mounting surface, a capillary structure with a curved portion, and a capillary inlet. The cartridge has a receiving surface, a cartridge inlet, a microfluidic structure, and a measurement structure. The method includes placing the blood sample into the capillary inlet; attaching the mounting surface to the receiving surface; rotating the cartridge about a rotational axis to transport the blood sample from the capillary structure to the cartridge inlet and into the microfluidic structure; controlling the rotation of the cartridge to process the blood sample into the processed sample using the microfluidic structure; controlling the rotation of the cartridge to transfer the processed sample to the measurement structure; and measuring the amount of the analyte using the measurement structure and a measurement system.

14 Claims, 13 Drawing Sheets

(51) Int. Cl.
- *G01N 1/28* (2006.01)
- *G01N 33/49* (2006.01)
- *G01N 21/07* (2006.01)
- *G01N 21/84* (2006.01)
- *B01L 3/00* (2006.01)
- *B01D 17/02* (2006.01)
- *A61B 5/15* (2006.01)
- *A61B 5/157* (2006.01)
- *A61B 10/00* (2006.01)

(52) U.S. Cl.
CPC .. *A61B 5/150022* (2013.01); *A61B 5/150213* (2013.01); *A61B 5/150221* (2013.01); *A61B 5/150343* (2013.01); *A61B 5/150358* (2013.01); *A61B 5/150755* (2013.01); *A61B 5/150832* (2013.01); *A61B 10/0045* (2013.01); *B01D 17/0217* (2013.01); *B01L 3/5021* (2013.01); *B01L 3/502753* (2013.01); *G01N 33/491* (2013.01); *B01L 2200/025* (2013.01); *B01L 2200/026* (2013.01); *B01L 2200/0631* (2013.01); *B01L 2200/10* (2013.01); *B01L 2300/043* (2013.01); *B01L 2300/0803* (2013.01); *B01L 2300/123* (2013.01); *B01L 2400/0406* (2013.01); *B01L 2400/0409* (2013.01); *G01N 21/07* (2013.01); *G01N 21/84* (2013.01); *G01N 2001/4083* (2013.01); *Y10T 436/2575* (2015.01); *Y10T 436/25375* (2015.01)

(58) Field of Classification Search
CPC ........ A61B 5/150221; A61B 5/150343; A61B 5/150358; A61B 5/150755; A61B 5/150832; A61B 5/157; B01D 17/0217; B01L 2200/025; B01L 2200/026; B01L 2200/0631; B01L 2200/10; B01L 2300/043; B01L 2300/0803; B01L 2300/123; B01L 2400/0406; B01L 2400/0409; B01L 3/5021; B01L 3/502753; G01N 1/4077; G01N 2001/4083; G01N 21/07; G01N 21/84; G01N 33/491; Y10T 436/25; Y10T 436/25375; Y10T 436/2575

USPC ........ 436/43, 45, 63, 174, 177, 180; 422/64, 422/68.1, 72, 501, 502, 503, 506, 527, 422/533; 435/287.3, 288.3, 288.5

See application file for complete search history.

(56) References Cited

U.S. PATENT DOCUMENTS

| | | | |
|---|---|---|---|
| 2009/0155925 A1* | 6/2009 | Boehm | B01F 1/0022 436/174 |
| 2009/0191643 A1 | 7/2009 | Boehm et al. | |
| 2014/0272941 A1* | 9/2014 | Gunnerson | B01L 3/50273 435/5 |
| 2014/0275866 A1* | 9/2014 | Gunnerson | A61B 5/14507 600/309 |
| 2014/0305823 A1* | 10/2014 | Gelfand | A61B 5/150305 206/363 |
| 2014/0309096 A1* | 10/2014 | Wilkinson | A61B 5/150305 494/43 |
| 2014/0309555 A1* | 10/2014 | Gelfand | A61B 5/150305 600/583 |
| 2018/0264471 A1* | 9/2018 | Boehm | B01L 3/5023 |

FOREIGN PATENT DOCUMENTS

| | | |
|---|---|---|
| JP | 2006068384 | 3/2006 |
| WO | 2006025608 A1 | 3/2006 |
| WO | 2014172235 A1 | 10/2014 |
| WO | 2014172247 A1 | 10/2014 |

OTHER PUBLICATIONS

Korean Office Action, dated Apr. 17, 2018, pertaining to KR Patent Application No. 10-2016-0173354 filed Dec. 19, 2016.

* cited by examiner

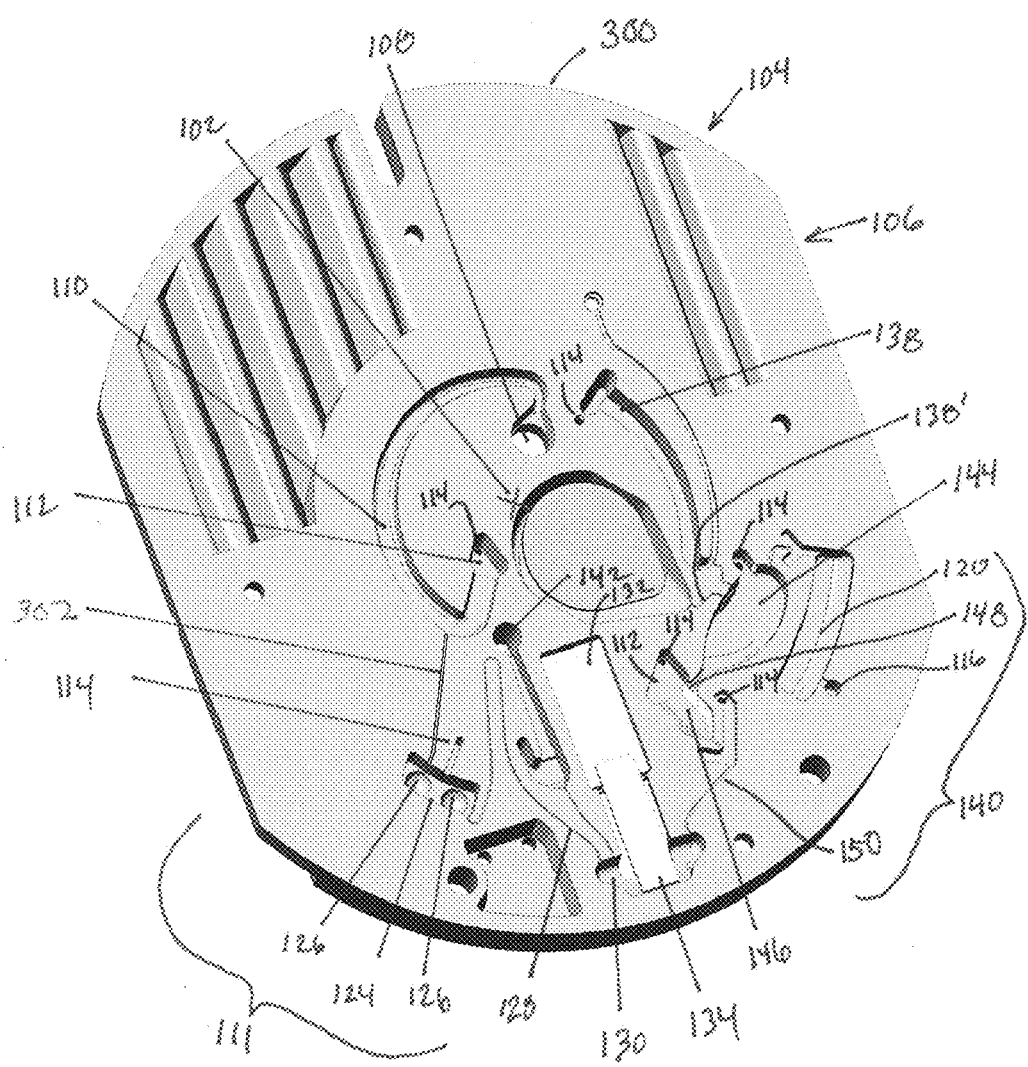

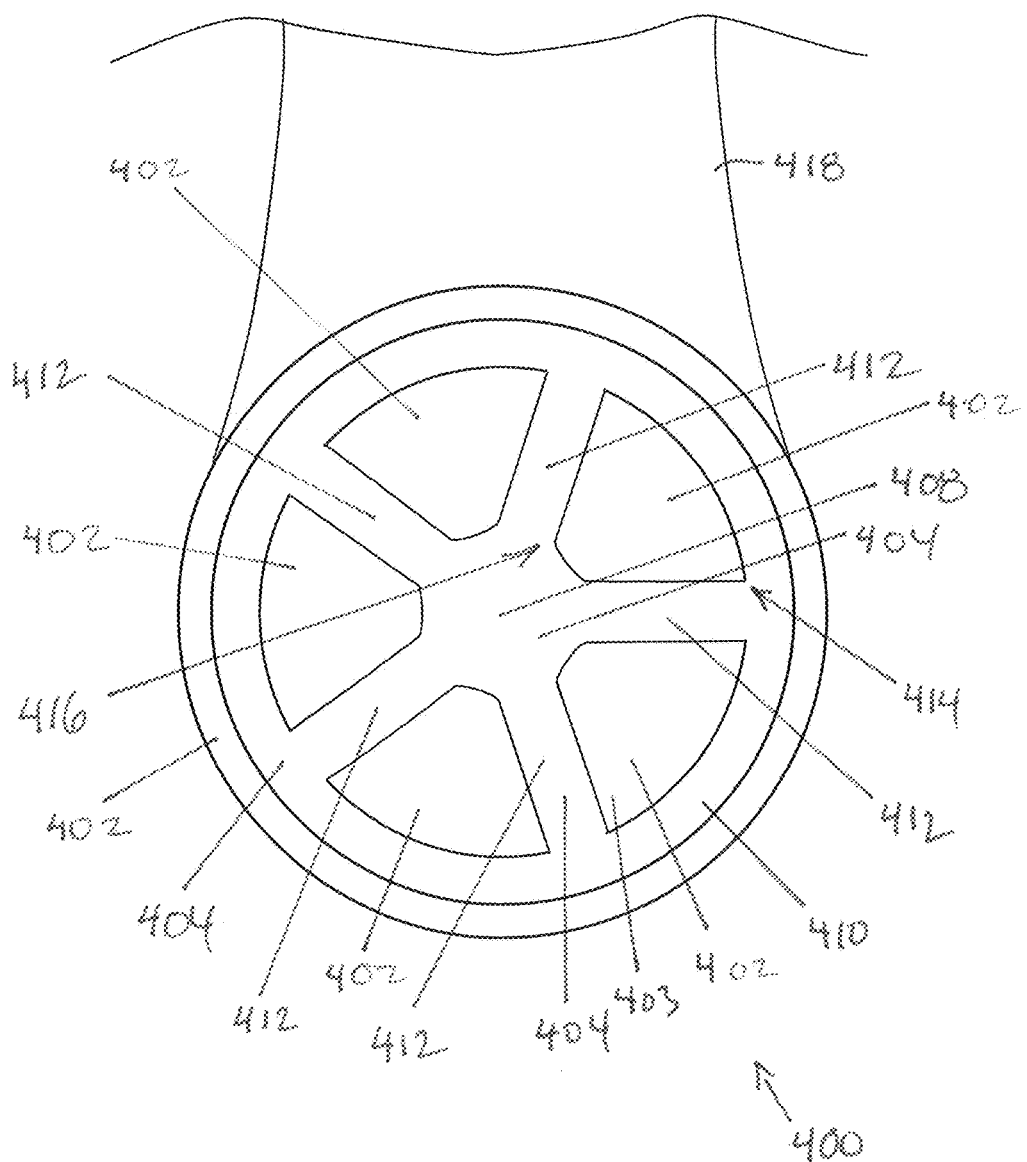

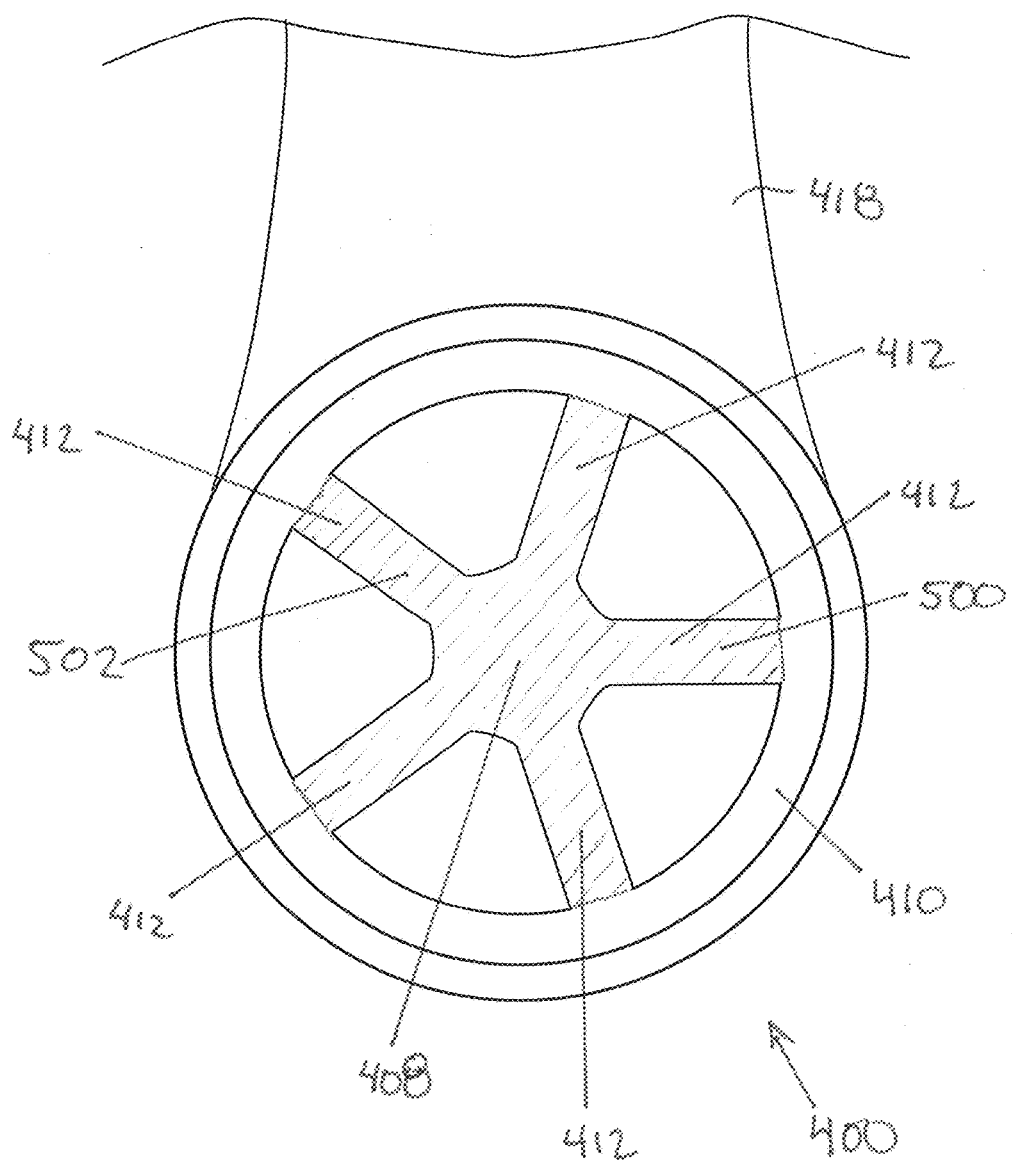

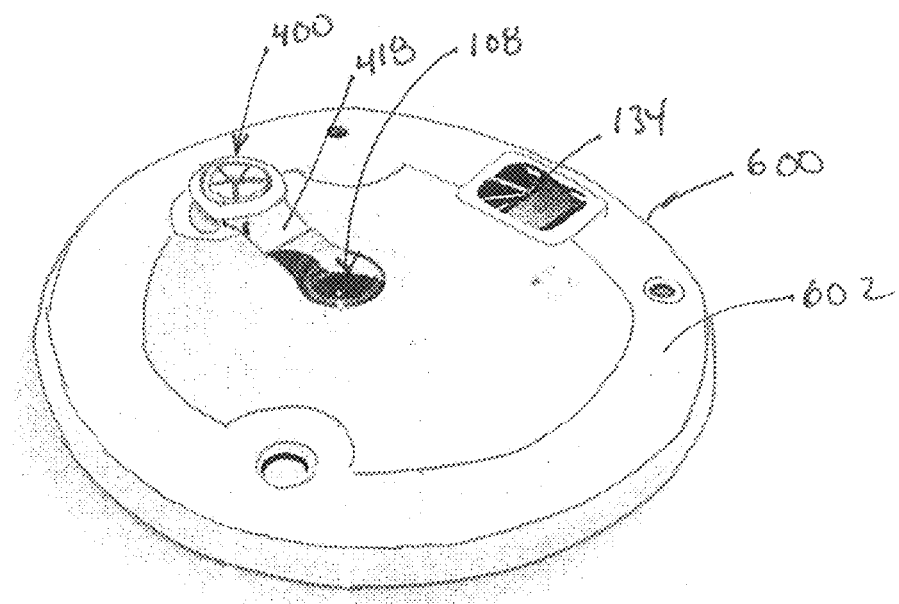
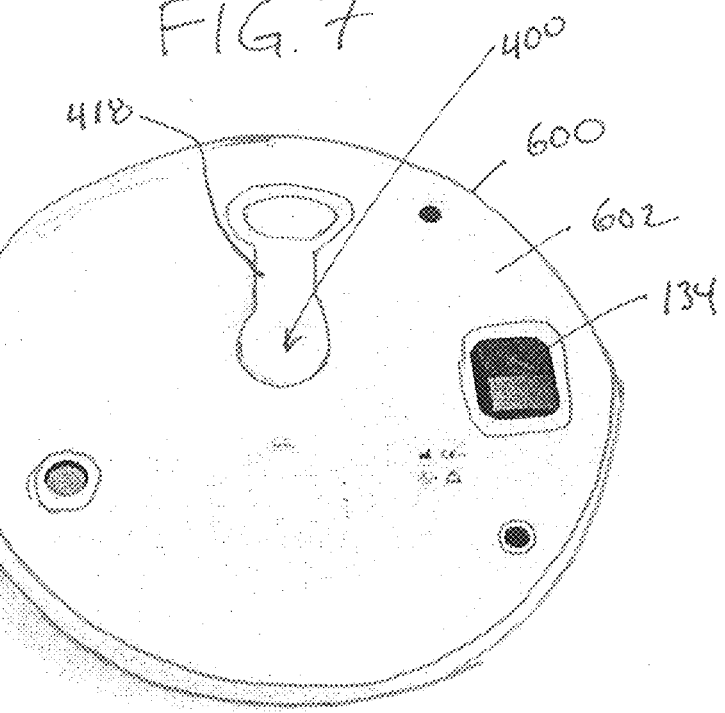

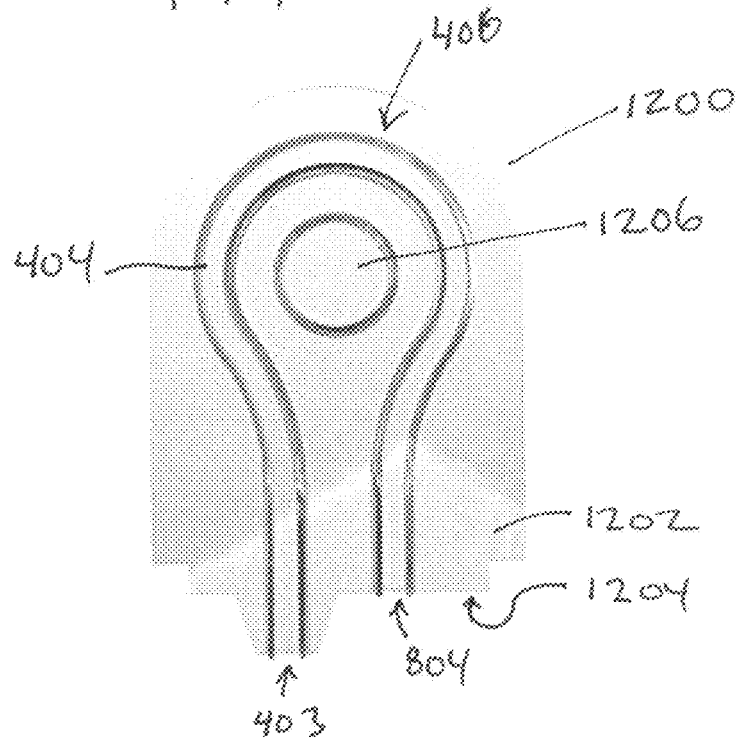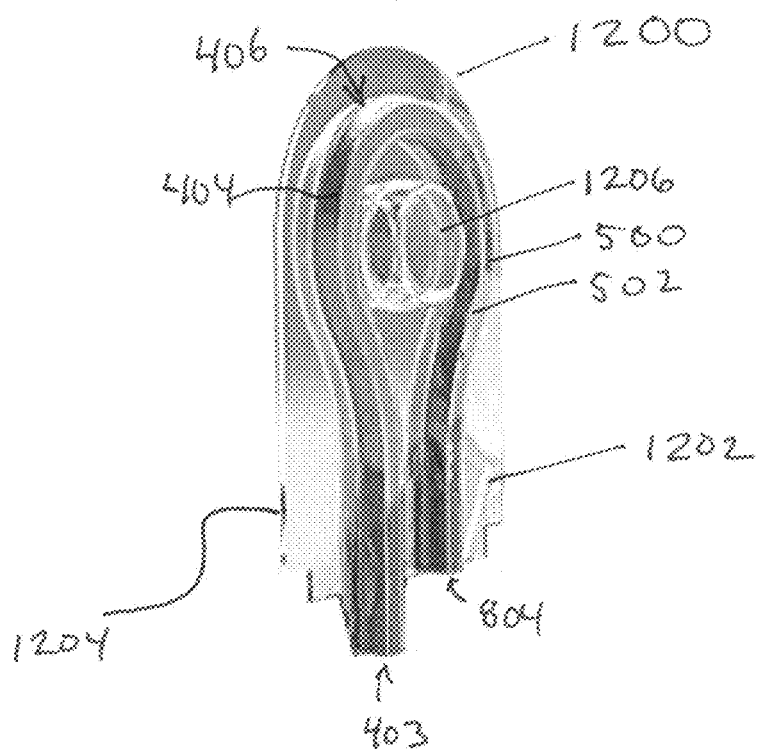

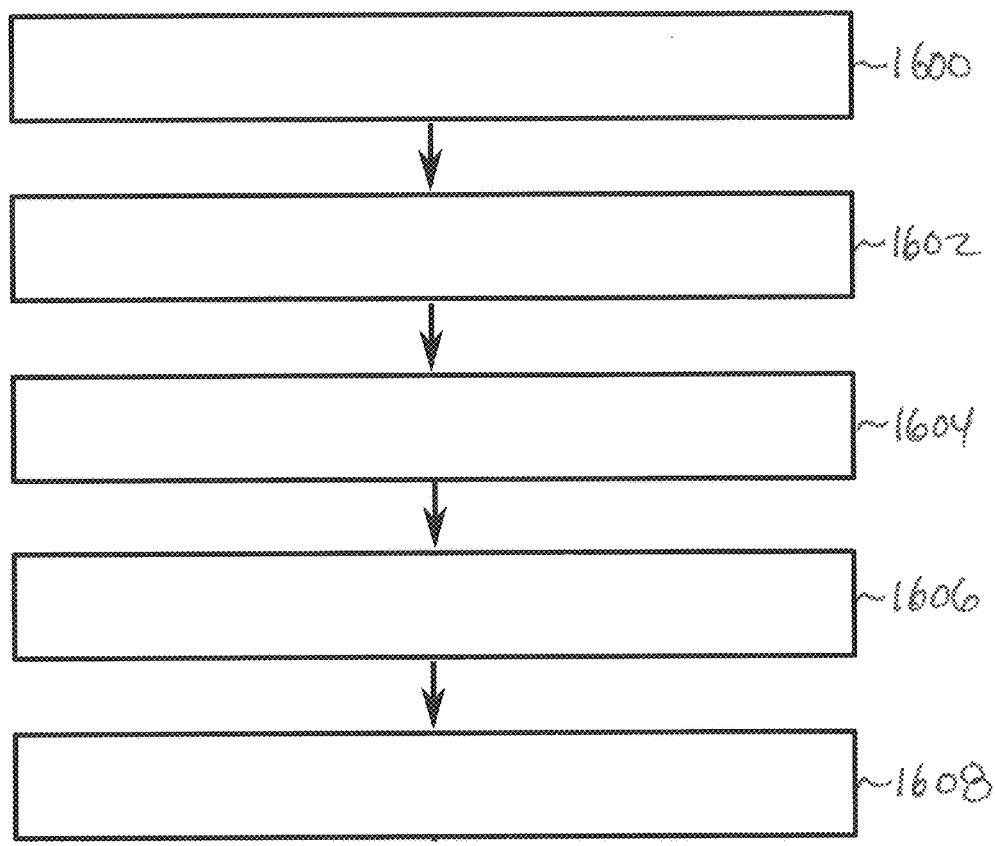

BLOOD COLLECTOR WITH CAPILLARY STRUCTURE

TECHNICAL FIELD

The inventive disclosure relates to analytical test devices for biological samples, in particular to the design and use of rotatable cartridges for performing a measurement of a blood sample.

BACKGROUND

Two classes of analysis systems are known in the field of medical analysis: wet analysis systems, and dry-chemical analysis systems. Wet analysis systems, which essentially operate using "wet reagents" (liquid reagents), perform an analysis via a number of required step such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis (also called point-of-care testing), for example, at resident physicians, on the wards of the hospitals, and in so-called "home monitoring" during the monitoring of medical-analytic parameters by the patient himself (in particular blood glucose analysis by diabetics or coagulation status by warfarin patients).

In wet analysis systems, the high-performance analysis instruments allow the performance of more complex multi-step reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the sample can first be brought in contact with a specific binding reagent for the analyte which is immobilized onto a surface. This can be achieved for example by mixing the sample with beads comprising surfaces with such immobilized reagents or transporting the sample over surfaces or through porous matrices wherein the surfaces or the porous matrices comprise coatings of the immobilized reagents. A marking reagent can subsequently be brought in contact with this surface in a similar manner to mark the bound analyte and allow its detection. To achieve a more precise analysis, a subsequent washing step is often performed, in which unbound marking reagent is at least partially removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control can be performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, increasingly are being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

United States patent application US 2009/0191643 A1 describes a test element and method for detecting an analyte with the aid thereof is provided. The test element is essentially disk-shaped and flat, and can be rotated about a preferably central axis which is perpendicular to the plane of the disk-shaped test element. The test element has a sample application opening for applying a liquid sample, a capillary-active zone, in particular a porous, absorbent matrix, having a first end that is remote from the axis and a second end that is near to the axis, and a sample channel which extends from an area near to the axis to the first end of the capillary-active zone that is remote from the axis.

SUMMARY

Embodiments of the invention provide for a method and a medical system in the independent claims. Additional embodiments are given in the dependent claims.

A cartridge as used here encompasses also any test element for processing a biological sample into a processed biological sample. The cartridge may include structures or components which enable a measurement to be performed on the biological sample. A typical cartridge is a test element as is defined and explained in U.S. Pat. No. 8,114,351 B2 and US 2009/0191643 A1 A cartridge as used herein may also be referred to as a Centrifugal microfluidic disc, also known as "lab-on-a-disc", lab-disk or a microfluidic CD.

A biological sample as used herein encompasses as chemical product derived, copied, replicated, or reproduced from a sample taken from an organism. A blood sample is an example of a biological sample that is either whole blood or a blood product. The blood plasma may be considered to be a processed biological sample.

It is understood that references to blood samples and products below and in the claims may be modified such that they refer to biological samples.

In one aspect, an embodiment of the invention provides for a method of determining an amount of an analyte in a blood sample using a cartridge and a blood collector. The cartridge is operable for being spun around a rotational axis.

The blood collector comprises a mounting surface. The blood collector further comprises a capillary structure for holding the blood sample. The capillary structure comprises a curved portion. Portions of the capillary structure may be straight but at least a portion of the capillary structure is curved. The blood collector further comprises a capillary inlet for receiving the blood sample. The blood collector can contain more than one inlet to receive samples from different sample sources (e.g. venous or capillary blood). For example the capillary inlet may be touched or placed adjacent to the blood sample and then the capillary force may draw the blood sample into the capillary structure through the capillary inlet.

The cartridge comprises a receiving surface for attaching to the mounting surface. The cartridge further comprises a cartridge inlet for receiving a blood sample from the blood collector. The blood collector is configured such that when the mounting surface is attached to the receiving surface the capillary inlet is positioned in fluidic connection with the cartridge inlet with the cartridge inlet. For example, the capillary inlet could be positioned at or in the cartridge inlet. In another example the capillary inlet could be positioned such that when the cartridge is rotated that the blood sample enters the cartridge inlet. For example, one could alternatively say that the blood collector is configured such that when the mounting surface is attached to the receiving surface the capillary inlet is positioned at the cartridge inlet or is positioned near the cartridge inlet.

The cartridge further comprises a microfluidic structure for processing the blood sample into a processed sample. The microfluidic structure is fluidically connected to the inlet. The cartridge further comprises a measurement structure for enabling measurement of the processed sample to determine the amount of the analyte in the blood sample.

The method comprises placing the blood sample into the capillary inlet. This may also be interpreted as placing the blood sample in contact with the capillary inlet. The capillary forces may then draw the blood sample through the capillary inlet into the capillary structure. The method further comprises attaching the mounting surface to the receiving surface. The method further comprises rotating the cartridge about the rotational axis to transport the blood sample from the capillary structure to the cartridge inlet. For example, the centrifugal force caused by rotating the cartridge and the blood collector around the rotational axis may force the blood sample out of the capillary structure and into the cartridge inlet. The method further comprises rotating the cartridge about the rotational axis to transport the blood sample from the cartridge inlet into the microfluidic structure. The method further comprises controlling the rotation of the cartridge about the rotational axis to process the blood sample into the processed sample using the microfluidic structure. The method further comprises controlling the rotation of the cartridge to transfer the processed sample to the measurement structure. The method further comprises measuring the amount of the analyte using the measurement structure and a measurement system.

The measurement structure may take different forms in different examples. For example in one example the measurement structure may be a chromatographic membrane with antibodies that attach to markers in the processed sample. Fluorescent markers may then be used to perform the measurement of the amount of the analyte. In other examples, the processed sample may be transported to an optically transparent container or region which may then be subjected to spectrographic measurements.

This embodiment may be beneficial because it may provide for an efficient means of providing a blood sample to the cartridge in order to perform the measurement of the amount of the analyte.

In another embodiment, the curved portion may be a capillary or a capillary tube.

In another embodiment, the curved portion may be a capillary stop.

In another embodiment, the blood sample is whole blood.

In another embodiment, the blood sample may be a serum.

In another embodiment, the blood sample may be a blood plasma.

In another embodiment, the sample may be urine.

In another embodiment, the microfluidic structure comprises a blood separation chamber for separating blood plasma or serum from the blood sample. The United States Patent US 2009/0191643 A1 illustrates a microfluidic structure in a rotational disc that is able to separate serum or plasma from the blood cell fraction (mainly the erythrocytes) of a whole blood sample.

The blood separation chamber is fluidically connected to the inlet. The method further comprises rotating the cartridge about the rotational axis to transport the blood sample from the cartridge inlet into the blood separation chamber. The method further comprises controlling the rotation of the cartridge about the rotational axis to separate the blood plasma from the blood sample by a centrifugation. The step of controlling the rotation of the cartridge about the rotational axis to process the blood sample into the processed sample using the microfluidic structure is performed such that the blood plasma is processed into the processed sample.

In another embodiment, the cartridge comprises an outer surface. Attaching the mounting surface to the receiving surface seals the cartridge inlet to the outer surface. For example, the blood collector may be in the form of a cap or other object which is then placed or snapped into the outer surface. It may be beneficial to seal the outer surface to reduce the chances of blood being splattered or spilled.

In another embodiment, the blood collector comprises a first snap element. The cartridge comprises a second snap element configured for engaging the first snap element to lock the mounting surface to the receiving surface. This may be beneficial because once the blood collector is attached to the cartridge it will stay fixed there. This may reduce the chance of the blood collector being placed haphazardly and spilling a portion of the blood sample. Additionally the blood collector and the cartridge form an integral component which can be disposed of at the same time. This may make it simpler for a user of the cartridge to dispose of both samples simultaneously. The use of the snaps may also prevent the cartridge from being used a second time. This for instance may prevent a blood sample being added to the cartridge two times, which may confuse the results of the measurement of the amount of the analyte.

In another embodiment, the blood collector is attached to the cartridge via a flexible element configured for guiding the mounting surface to the receiving surface. For example the blood collector may be in the form of a cap. Using the flexible element may be beneficial because it may help reduce the chance of losing or misplacing the blood collector.

In another aspect, another embodiment of the invention provides for a medical system comprising a blood collector. The blood collector comprises a mounting surface for attaching to a receiving surface of a cartridge. The blood collector further comprises a capillary structure for holding the blood sample. The capillary structure has a curved portion. The blood collector further comprises a capillary inlet for receiving the blood sample into the capillary structure. This embodiment may be beneficial because it provides a unit, which can be attached to the cartridge and can deliver blood to the cartridge in a compact fashion.

In another embodiment, the capillary structure forms at least a part of a visual indicator for indicating when the capillary structure is filled with the blood sample. Incorporating the visual indicator into the capillary structure may be useful because this may help to ensure that the blood sample has a sufficient volume when the measurement is performed. In some examples, the capillary structure itself may be transparent or open and this may provide a means of visual inspection which allows an operator or user to see if the blood sample volume is large enough for the analysis to be performed.

In another embodiment, the blood collector has a fluidic layout which enables the emptying of the capillaries by centrifugal force when spun around the rotational axis.

In another embodiment, the blood collector comprises a vent for venting the capillary structure. For example, the capillary structure may have a capillary inlet and at an opposing or opposite end or other portion the capillary structure may have a vent. This may enable the centrifugal forces to drain blood from the capillary structure.

In another aspect the invention provides for a medical system further comprising a cartridge. The cartridge is operable for being spun around a rotational axis. The cartridge comprises a receiving surface. The cartridge further comprises a cartridge inlet for receiving the blood sample from the blood collector. The blood collector is configured such that when the mounting surface is attached to the receiving surface the capillary inlet is positioned at the cartridge inlet. The cartridge further comprises a microfluidic structure for processing the blood sample into a processed sample. The microfluidic structure is fluidically connected to the inlet. The cartridge further comprises a measurement structure for enabling measurement of the processed sample to determine the amount of the analyte in the blood sample. This embodiment may be beneficial because the cartridge and the blood collector may provide for a means of dispensing a proper amount or dose of blood for measurement.

In another embodiment, the cartridge comprises an outer surface. Attaching the mounting surface to the receiving surface may for instance seal the cartridge inlet to the outer surface.

In another embodiment, the microfluidic structure comprises a blood separation chamber for separating blood plasma from the blood sample. The blood separation chamber is fluidically connected to the inlet. This embodiment may be beneficial because it may provide a means of producing blood plasma from a whole blood sample.

In another embodiment, the blood collector comprises a first snap element.

In another embodiment, the cartridge comprises a second snap element configured for engaging the first snap element to lock the mounting surface into the receiving surface.

In another embodiment, the capillary structure is formed from rigid plastic. The capillary inlet is perpendicular to the capillary structure. The capillary inlet extends beyond the mounting surface. The blood collector comprises a finger grip. This embodiment may be beneficial because it may provide an efficient means of inserting a capillary structure into the cartridge.

In another embodiment, the first snap element extends beyond the mounting surface.

In another embodiment, the blood collector snaps onto a central region of the cartridge so that the cartridge is balanced during rotation. This may be beneficial if the cartridge is to be spun at a higher rotational rate around the rotational axis.

In another embodiment, the capillary inlet is off of the rotational axis when the blood collector has been snapped onto the central region. This may make it easier to centrifuge the blood out of the capillary structure.

In another embodiment, the blood collector is attached to the cartridge via a flexible element configured for guiding the mounting surface to the receiving surface. This may be beneficial for aligning the blood collector so that the mounting surface mates properly with the receiving surface.

In another embodiment, the blood collector comprises an exposed surface. The capillary structure is formed as open channels in the exposed surface. The capillary inlet is formed where the open channels meet the exposed surface.

The open channels comprise a connected outer channel. The channels further comprise a central region. The channels further comprise spoke channels. The spoke channels connect the central region to the outer connected channel. The connected outer channel forms a capillary stop for the spoke channels. This embodiment may be beneficial because it may provide for a compact and easily visually inspected blood collector.

In another embodiment, the connected outer channel is circular. The connected outer channel may be the portion. The capillary stop may form part of the capillary structure therefore.

In another embodiment, the boundary between the connected outer channel and the spoke channels forms sharp edges. This may be beneficial in forming the capillary stop.

In another embodiment, the boundary between the central region of the spoke channels is rounded or smooth. This may aid the flow of blood from the central region to the spoke channels.

In another embodiment, the blood collector comprises a foil portion. The blood collector further comprises a formed portion. The formed portion is plastic. The capillary structure and the capillary inlet are formed in the formed portion. The curved portion is parallel to a plane. The foil portion is parallel to the plane. The foil portion forms a wall of the capillary structure.

The term thermoformed may for instance refer to blow molded, deep drawn, or embossed.

In another embodiment, the blood collector further comprises an elevated finger grip. The elevated finger grip is formed from the thermoformed portion. The capillary structure extends to a first distance from the foil portion. The elevated finger grip extends to a second distance from the foil portion. The second distance is greater than the first distance. This may enable easier gripping of the blood collector.

In another embodiment, the curved portion at least partially surrounds the elevated finger hole. This may be useful in making the blood collector more compact.

In another embodiment, the elevated finger hole could be used to align the blood collector in the cartridge. For example there may be a recess in the cartridge which receives the finger hole. In this respect this may be beneficial because the finger hole may be useful for both holding the blood collector during the collection of the blood sample and also for placing or locking it into the cartridge.

In another embodiment, the mounting surface is parallel to a plane.

In another embodiment, the capillary structure is parallel to the plane.

In another embodiment, the medical system further comprises a cartridge spinner for controlling the rotation of the cartridge about the rotational axis. This may be beneficial when rotating the cartridge around the rotational axis so that it can be performed in an automated fashion.

In another embodiment, the medical system comprises a memory for storing machine-executable instructions in a processor for controlling the medical system. Execution of the machine-executable instructions causes the processor to rotate the cartridge about the rotational axis to transport the blood sample in the capillary structure to the cartridge inlet by controlling the cartridge spinner. Execution of the machine-executable instructions further causes the processor to rotate the cartridge about the rotational axis to transport the blood sample from the cartridge inlet to the microfluidic structure by controlling the cartridge spinner. Execution of the machine-executable instructions further causes the processor to control the rotation of the cartridge about the rotational axis to process the blood sample into the processed sample using the microfluidic structure by controlling the cartridge spinner. Execution of the machine-executable instructions further causes the processor to control the rotation of the cartridge to transfer the processed sample to the measurement structure by controlling the cartridge spinner. Execution of the machine-executable instructions further causes the processor to measure the amount of the analyte using the measurement structure and a measurement system.

In another embodiment, execution of the machine-executable instructions further causes the processor to rotate the cartridge about the rotational axis to transfer the blood sample from the cartridge inlet into a blood separation chamber by controlling the cartridge spinner. Execution of the machine-executable instructions further causes the processor to control the rotation of the cartridge about the rotational axis to separate blood plasma from the blood sample by centrifugation by controlling the cartridge spinner. Execution of the machine-executable instructions further causes the processor to control the rotation of the cartridge about the rotational axis to process the blood plasma into the processed sample using the microfluidic structure by controlling the cartridge spinner.

BRIEF DESCRIPTION OF THE DRAWINGS

In the following embodiments, the various disclosed embodiments of the invention are explained in greater detail, by way of example only, making reference to the drawings in which:

FIG. 3 shows a front view of part of an alternative cartridge;
FIG. 4 illustrates an example of a blood collector;
FIG. 5 shows the blood of collector of FIG. 4 when filled with blood;
FIG. 6 shows the blood collector of FIG. 4 being used with a cartridge;
FIG. 7 further shows the blood collector of FIG. 4 being used with a cartridge;
FIG. 12 illustrates a further example of a blood collector;
FIG. 13 further illustrates the blood collector of FIG. 12;
FIG. 16 shows a flow chard which illustrates a method of operating the blood collector of FIG. 15.

DETAILED DESCRIPTION

Like numbered elements in these figures are either equivalent elements or perform the same function. Elements which have been discussed previously will not necessarily be discussed in later figures if the function is equivalent.

The cartridge, for example, may be made or formed out of plastic with a cover attached. The microfluidic structures may, in some examples, be formed by the formed plastic piece and a cover.

Figure 1:
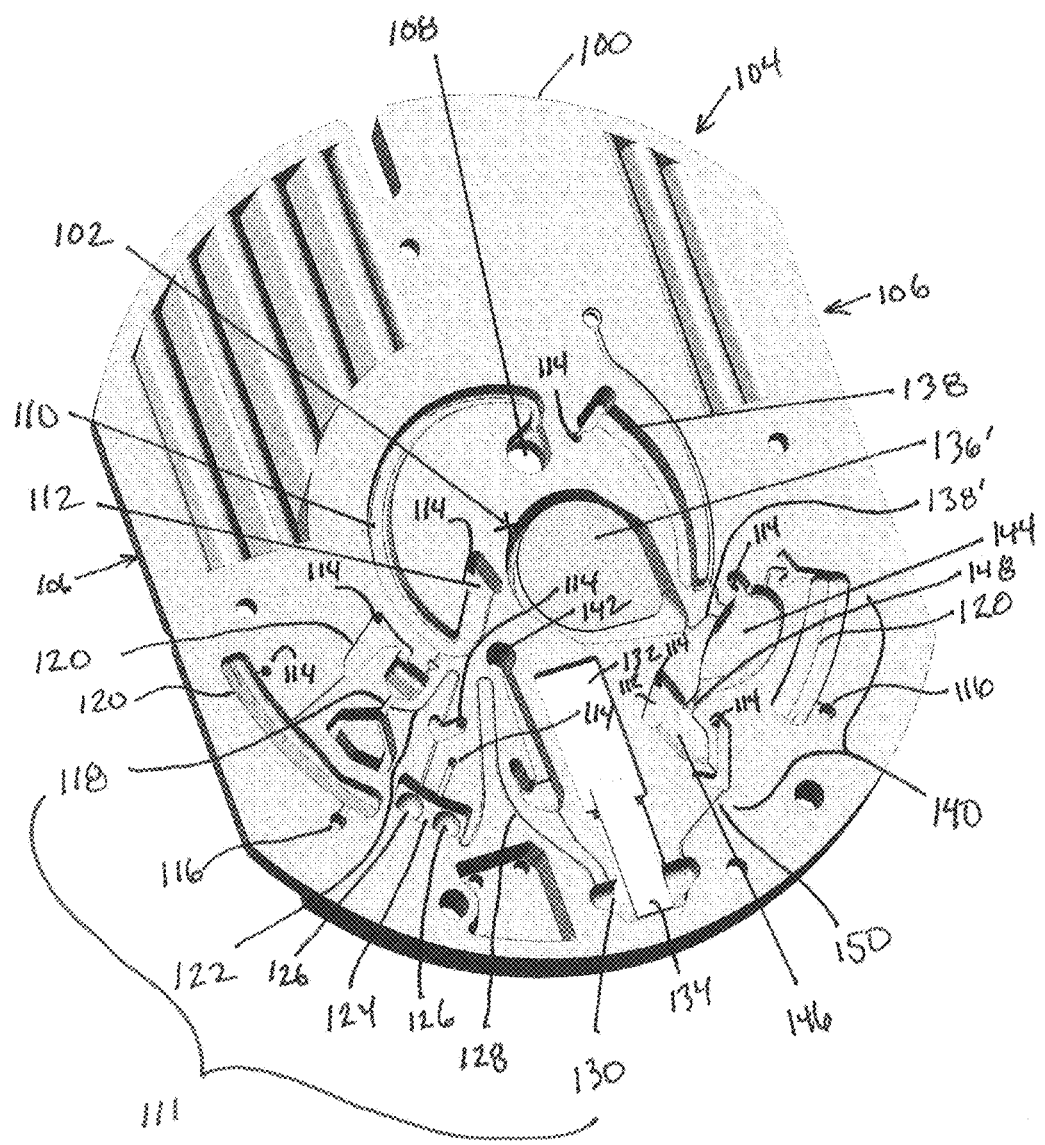
FIG. 1 shows a front view of part of a cartridge.
Figure 2:
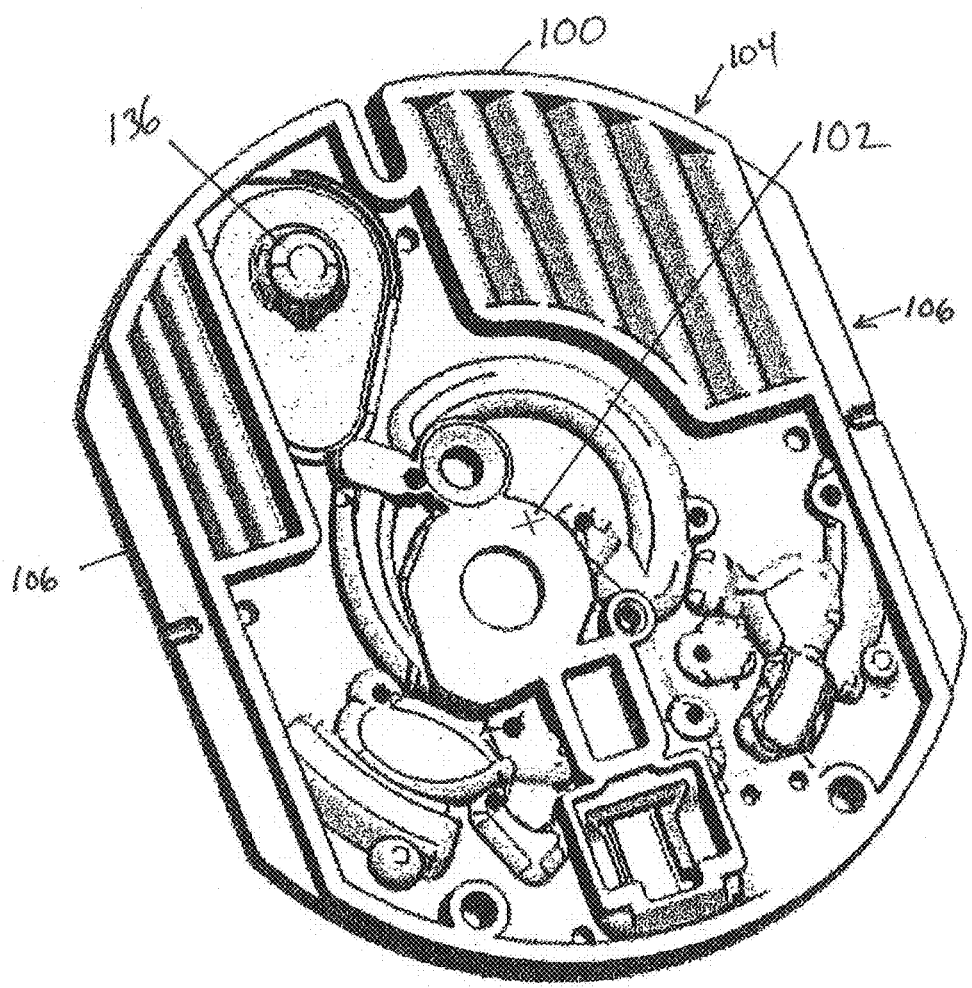
FIG. 2 shows a rear view of the cartridge of FIG. 1.

FIG. 1 shows a portion of a cartridge 100 without the outer cover surface. FIG. 1 is a front view and FIG. 2 is a rear or back view. As such the receiving surface of the cartridge is not shown in FIGS. 1 and 2. FIG. 1 shows a cartridge inlet 108 that is connected to a microfluidic structure 111, 111'. The microfluidic structure 111 in this example is used for processing whole blood into plasma and then to generate a processed sample which is then transported across a measurement structure 134. In this example the measurement structure is a chromatographic membrane. There is an additional microfluidic structure 111' which may be used for providing multiple aliquotions of washing fluid for washing the chromatographic strip 134. The microfluidic structure 111 and the measurement structure 130 as shown in FIGS. 1 and 2 are exemplary. The microfluidic structure 111 and the measurement structure 130 may vary depending upon the type of measurement to be performed on the analyte.

FIG. 1 shows a front view of the cartridge 100. FIG. 2 shows a backside view of the cartridge 100. The cartridge is adapted for rotating around a rotational axis 102. The cartridge 100 is predominantly flat and has an outer edge perpendicular to the rotational axis 102. The outer edge 104 is less than a particular radius and is predominantly circular in shape. In the embodiment shown in FIGS. 1 and 2, there are also several optional flat portions 106 of the outer edge. These may aid in gripping or storing the cartridge 100. In alternative embodiments such flat portions are lacking and the overall outer edge of the cartridge is predominantly circular in shape. The cartridge 100 could for example be made out of molded plastic. There may be a cover which is placed on the surface of the structure shown in FIG. 1. The cover is not shown so as to aid the view of the microfluidic structure within the cartridge 100.

The cartridge 100 is shown as having a cartridge inlet 108 where a blood sample can be added or pipetted into the cartridge 100. The cartridge inlet 108 may for example comprise a storage chamber 110 for storing a volume of a blood sample. The storage chamber 110 is shown as having an expansion chamber 112 with a vent 114. The various microfluidic structures may be shown as having expansion chambers 112 and vents 114 also. There may also be failsafe indicators 116 which are regions of the microfluidic structure which fill with fluid to indicate that a microfluidic structure has received a sufficient amount of fluid or sample. These for example may be checked optically during the use of the cartridge 100. These in some cases are labeled but are not discussed herein. The cartridge inlet 108 is shown as being fluidically connected to a blood separation chamber 118. The blood separation chamber 118 is used to separate the plasma from the corpuscular blood sample components (blood cells) in a blood sample. The blood separation chamber 118 is shown as also being connected to an overflow chamber 120 that accepts an excess of plasma from the blood sample. The functioning of the blood separation chamber 118 will be described in more detail below. The blood separation chamber 118 is connected to a processing chamber 124 via a first valve structure 122.

In this example the first valve structure 122 is a siphon. It could however include other structures such as a mechanical, magnetic, or thermally activated valve. The processing chamber 124 is shown as containing several surfaces 126 which could be used for storing a dry reagent. In other examples there may be amounts of liquid or other types of reagent which can be mixed with a plasma sample. The processing chamber 124 is shown as being connected to a measurement structure 130 via a second valve structure 128. In this example the second valve structure 128 is a siphon. The second valve structure 128 could take any of the forms that the first valve structure 122 can also take. In this example the processing chamber 124 is shown as being a single chamber. In another example the processing chamber 124 may comprise several sub-chambers so that a plasma sample can be processed by different reagents sequentially. The measurement structure 130 is shown as containing a chromatographic membrane 134 and in contact with the rotational axis-nearer end of the chromatographic membrane an additional absorbent structure 132 which serves as a waste fleece. The reagents and the chromatographic membrane 134 are discussed in greater detail below.

After being processed with a reagent the plasma sample may be wicked or transported across the chromatographic membrane 134. Before and/or after a washing buffer may be used to prime or wash the chromatographic membrane 134. The cartridge 100 shown in FIGS. 1 and 2 is a cartridge which incorporates a number of distinct optional features. On the backside of the cartridge 100 is shown a fluid chamber 136. In this example the fluid chamber 136 is a blister pack or flexible fluid chamber which can be opened from outside of the cartridge 100. For example, the blister pack may be compressed to be opened. However other mechanisms or methods may also be used to open the blister pack. When the fluid chamber 136 is compressed a seal is broken which allows fluid within the fluid chamber 136 to enter a fluid duct 138. The fluid duct 138 then transports fluid to a metering structure 140.

The metering structure 140 enables the washing buffer to be supplied to the measurement structure 130 multiple times in precisely measured amounts. The metering structure 140 is however not necessary. There may be examples where the washing buffer is delivered directly to the measurement structure 130. In other examples the measurement structure is not primed with the washing buffer before the test is performed. The structure labeled 136' is an alternate fluid chamber. The fluid chamber 136' may be mechanically actuated to break a seal around its perimeter which causes fluid to enter the metering structure 140 via the fluid duct 138'. The cartridge 100 is also shown as containing another optional structure. The structure labeled 142 is a manual fill location where a reagent or buffer solution may be added manually to the measurement structure 130 or by an external source like a dispenser.

The metering structure 140 is shown as containing an aliquoting chamber 144. The aliquoting chamber 144 receives the fluid from the fluid chamber 136 or 136'. The aliquoting chamber 144 is connected to a metering chamber 146 via a connecting duct 148. The metering structure 146 is used to accurately meter the buffer fluid and supply metered aliquots of the fluid one or more times to the measurement structure 130. The metering structure 146 is connected to the measurement structure 130 via a fluidic element 150. In this case the fluidic element 150 is shown as containing a microfluidic duct or channel and a chamber for holding a quantity of the buffer fluid as it is being metered. The function of the metering structure 140 and several alternatives will be discussed with reference to later Figs.

FIG. 3 shows an alternative cartridge 300. The cartridge in FIG. 3 is similar to the cartridge of FIG. 1 except the microfluidic structures for processing whole blood into plasma are not present. The storage chamber 110 is connected directly to the processing chamber 124 via a fluid duct 302. The cartridge 300 may be used for processing other types of blood samples into the processed sample such as serum or blood plasma. The example in FIG. 3 is representative. For example, a metering chamber could be added between the storage chamber 110 and the processing chamber 124 so that a defined amount of fluid is passed into the processing chamber.

FIG. 4 shows an example of a blood collector 400. The blood collector has an exposed surface 401 that is identical with a mounting surface 402. Recessed into the mounting surface 402 is a capillary structure 404. The capillary structure 404 has a curved portion 406. In the center there is a central region 408. There is an outer channel 410 which is identical with the curved portion 406. The outer channel 410 forms a capillary stop. There are five spoke channels 412 which are shown as connecting the central region 408 with the outer channel 410. Where the spoke channels 412 meet the outer channel 410 there are sharp edges 414. These sharp edges and the outer channel 410 form the capillary stop to keep the blood sample within the central region 408 and the spoke channels 412. Where the spoke channels 412 meet the central region 408 there are rounded edges 416. This facilitates filling of the complete spoke channels 412 and the central region 408. The blood collector 400 is connected to a flexible element 418. For instance the flexible element 418 could be connected to a cover of the cartridge. During use a finger prick with a blood droplet may be place approximately over the central region 408. The capillary action in the spoke channels 412 will cause the blood to be drawn into the capillary structure 404.

FIG. 5 shows the blood collector 400 after blood has been used to fill the capillary structure. In FIG. 5 the central region 408 and the spoke channels 412 have been filled with a blood sample 500. The blood 500 in the capillary structure forms a visual indicator 502 to indicate when the blood sample 500 has a sufficient volume. It can be seen that the blood sample 500 remains within the central region 408 and the spoke channels 412. The outer channel 410 does not contain blood and functions as the capillary stop.

FIG. 6 shows an example of a cartridge 600 with a blood collector 400 as is shown in FIGS. 4 and 5. It can be seen that a flexible element 418 connects the blood collector 400 to the cartridge 600. The cartridge 600 may for example use the internal cartridge portions shown in FIG. 1 or 3. The measurement structure 134 is visible through a window. The cartridge inlet 108 is shown as being open and exposed to an outer surface 602 of the cartridge 600. In practical use a subject could have a finger prick and then place the drop of blood on the blood collector 400. After it is apparent that enough blood has been collected such as shown as in FIG. 5 the blood collector 400 can simply be folded onto the cartridge inlet 108. The flexible element 418 controls the path of the blood collector 400 such that it seals perfectly. In some examples the seal may be airtight, in other examples the seal may not be airtight. However, closing the blood collector 400 on the cartridge inlet 108 may help prevent the splattering of blood. Sealing the cartridge 600 may also make it more convenient for safe disposal.

FIG. 7 shows the blood collector 400 after it has been folded and closed onto the cartridge inlet 108. It can now be seen that the cartridge inlet 108 is sealed or isolated from the outer surface 602.

Figure 8:
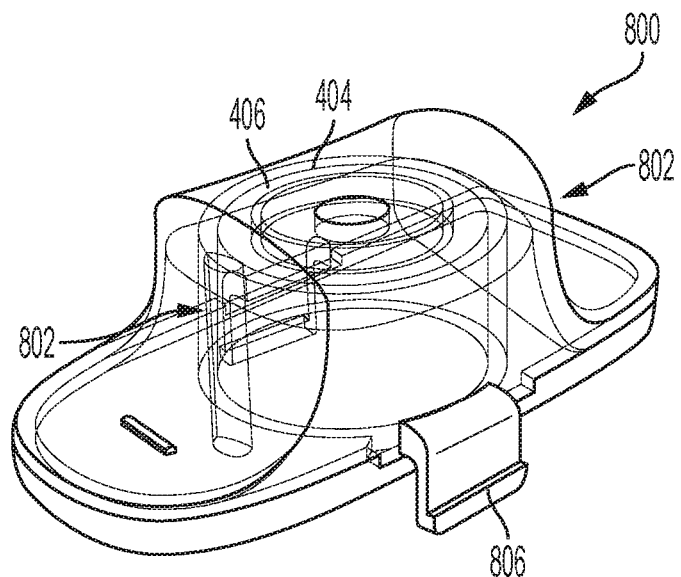
FIG. 8 illustrates a further example of a blood collector.
Figure 9:
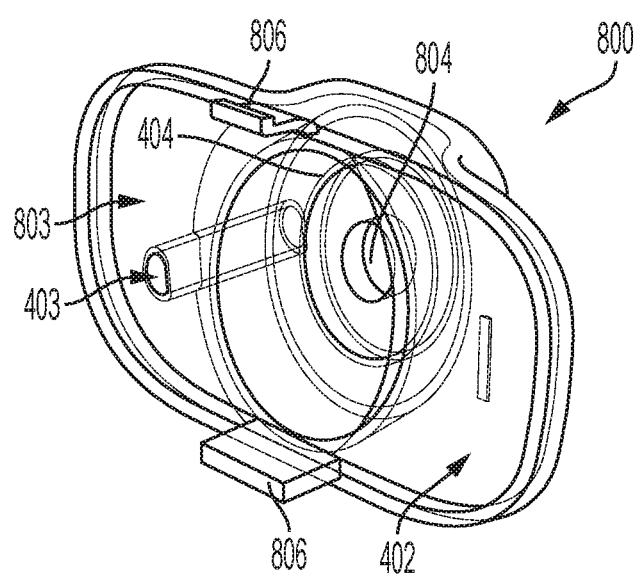
FIG. 9 further illustrates the blood collector of FIG. 8.
Figure 10:
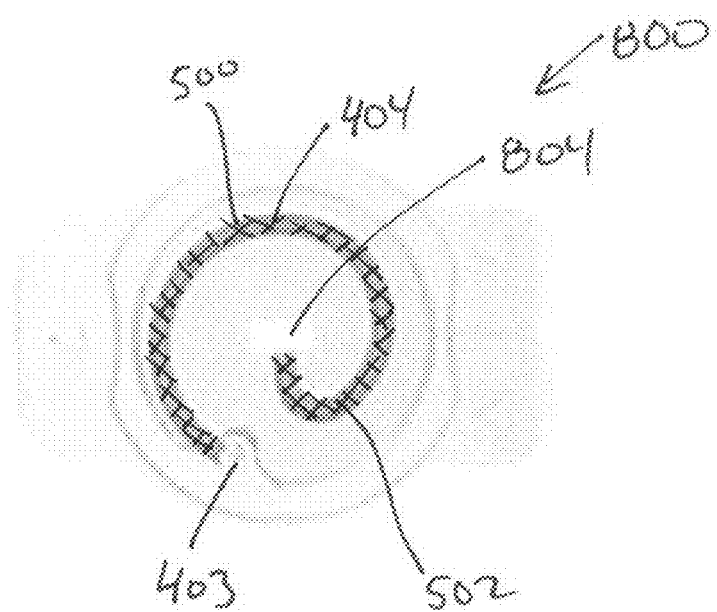
FIG. 10 further illustrates the blood collector of FIG. 8.

FIGS. 8, 9 and 10 show a further example of a blood collector 800. FIG. 8 shows a perspective view which illustrates the top of the blood collector 800. FIG. 9 shows another perspective view which shows the bottom of the blood collector 800. FIG. 10 shows a bottom view of the blood collector 800. The blood collector 800 is made of transparent molded plastic. The blood collector 800 is in the form of a small plastic piece with finger grips 802 that enable a person to precisely hold the blood collector 800. The capillary inlet 403 is a tube which extends beyond a lower surface 803. The capillary inlet 403 connects with a capillary structure 404 which is a curved capillary tube in the top of the blood collector 800. The capillary structure 404 has two connections to the atmosphere, one is the capillary inlet 403 and the other is a vent 804 which is also in the top. The blood collector 800 is designed to be snapped into a cartridge. There are two first snap elements 806. These snap elements 806 may fit into slots on the outer surface of a cartridge. The slots would form a second snap element. When the blood collector 800 is snapped into the surface the blood collector 800 is then not able to be removed without the use of tools. In FIG. 10 the capillary structure 404 is shown as being filled with the blood sample 500. The vent 804 forms a capillary stop which then fills the capillary structure 404 with a precise amount of the blood sample.

Various alternatives to the example shown in FIGS. 8, 9, and 10 may also be made. In FIGS. 8, 9, and 10, the capillary inlet 403 is to the side and the vent 804 is located at the center of the blood collector 800. In an alternative, the positions of the capillary inlet 403 and the vent 804 can be switched.

Figure 11:
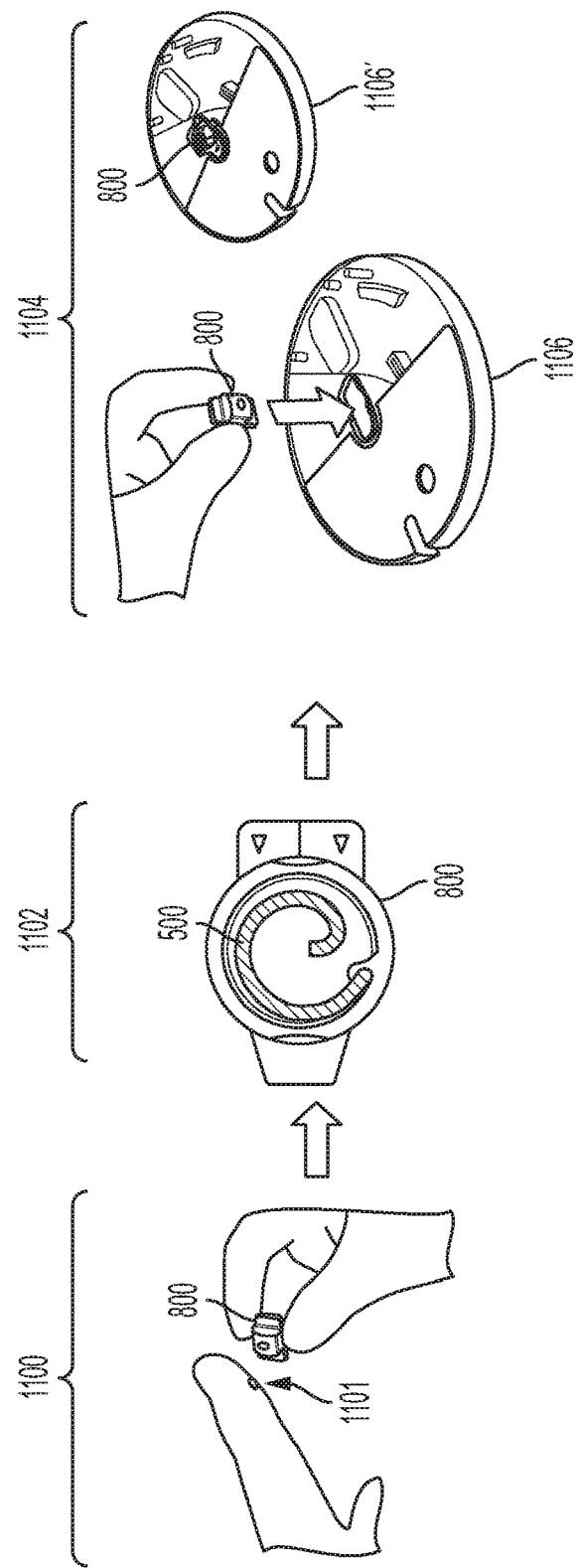
FIG. 11 illustrates the use of the blood collector of FIG. 8.

FIG. 11 graphically illustrates a method of using the blood collector 800 shown in FIGS. 8, 9 and 10. First in step 1100 the capillary inlet 403 of the blood collector 800 is brought into contact with a drop of blood 1101 caused by a finger prick. Next in step 1102 the blood collector 800 is visually inspected to see that the blood sample 500 fills the entire capillary structure. Next in step 1104 the blood collector 800 is snapped onto a cartridge 1106. Cartridge 1106' shows the blood collector 800 mounted. The first snap elements 806 go into grooves on the cartridge 1106 which are not visible in this Fig. This causes the blood collector 800 to be permanently attached to the cartridge 1106'.

FIGS. 12 and 13 show a further example of a blood collector 1200. The blood collector 1200 in FIG. 12 shows a top view. The view in FIG. 13 shows a perspective side view. The blood collector 1200 is formed from two portions, a first formed portion 1202 and a second formed portion 1204. The first formed portion and/or the second formed portion may be made from a foil. For example the first formed portion may be made from a plastic foil which may be thermoformed. The second formed portion may for example be a metal or Mylar type foil. The second formed portion may in some examples also be referred to as a foil portion. The illustrated structure is similar to blister pack packaging where the first formed portion 1202 is out of formed plastic foil. This creates depressions in the formed portion 1202 that are then sealed in the back with a foil 1204. In the center of the blood collector 1200 is an elevated finger grip 1206 which makes it easier to grip and to hold the blood collector 1200. Within the first formed portion 1202 is a capillary structure 404. This is essentially a capillary tube which wraps around the elevated finger hole 1206 and has a curved portion 406. The capillary structure 404 has a capillary inlet 403 and a vent 804. In use an operator can hold the blood collector 1200 by the elevated finger grip 1206 and bring the capillary inlet 403 in contact with blood or a blood product.

FIG. 13 shows the capillary structure 404 filled with blood 500. This forms a visual indicator 502 to indicate when the blood sample has been completely collected.

Figure 14:
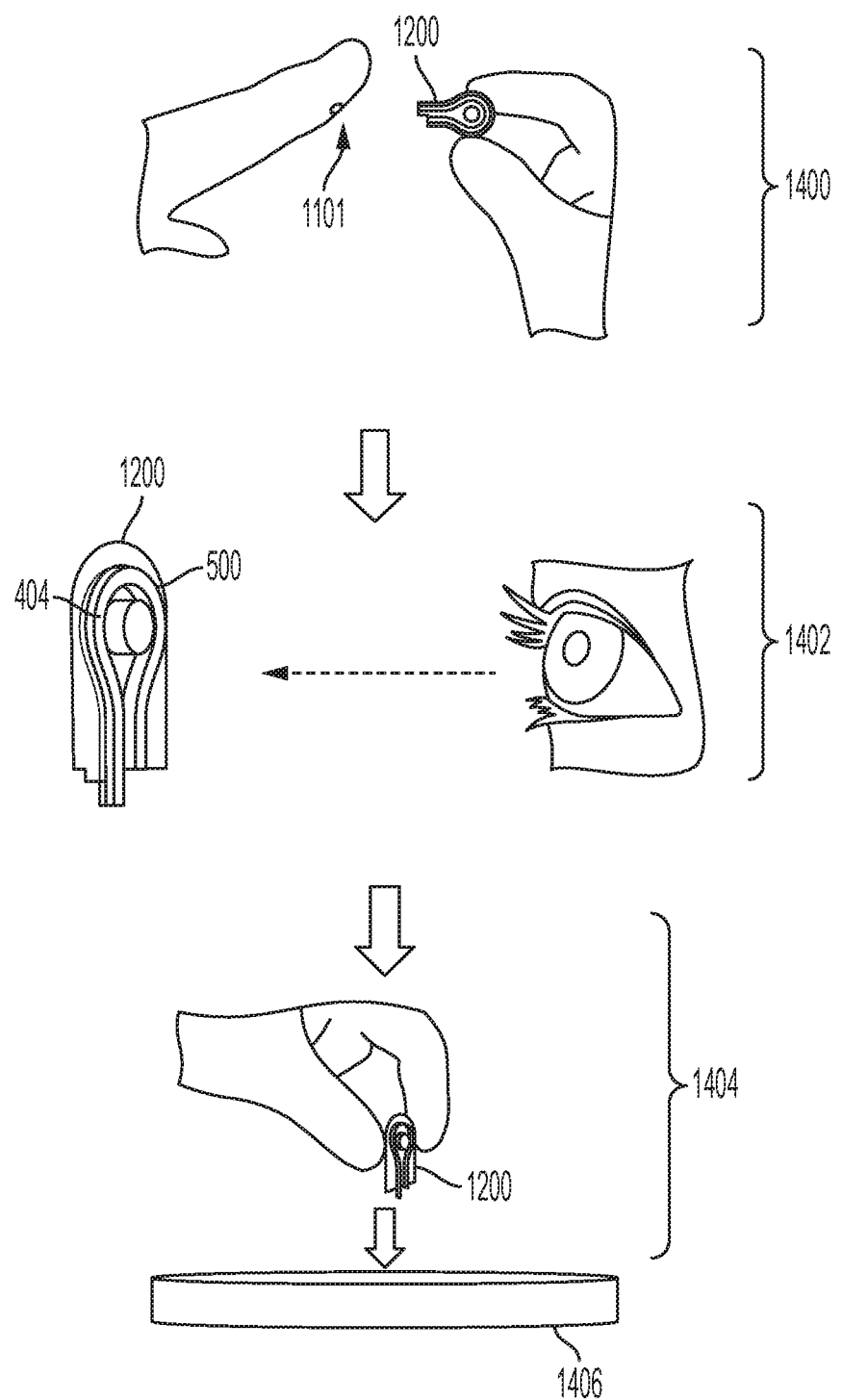
FIG. 14 illustrates the use of the blood collector of FIG. 12.

FIG. 14 visually illustrates the use of the blood collector 1200. First the capillary inlet of the blood collector 1200 is brought into contact with a blood drop 1101 on a finger prick. Next in step 1402 the blood collector 1200 is visually inspected to see if the blood 500 completely fills the capillary structure 404. In step 1404 the blood collector 1200 is inserted into a cartridge 1406. The cartridge 1406 may for instance have a depression or space into which the blood collector 1200 can be placed.

Figure 15:
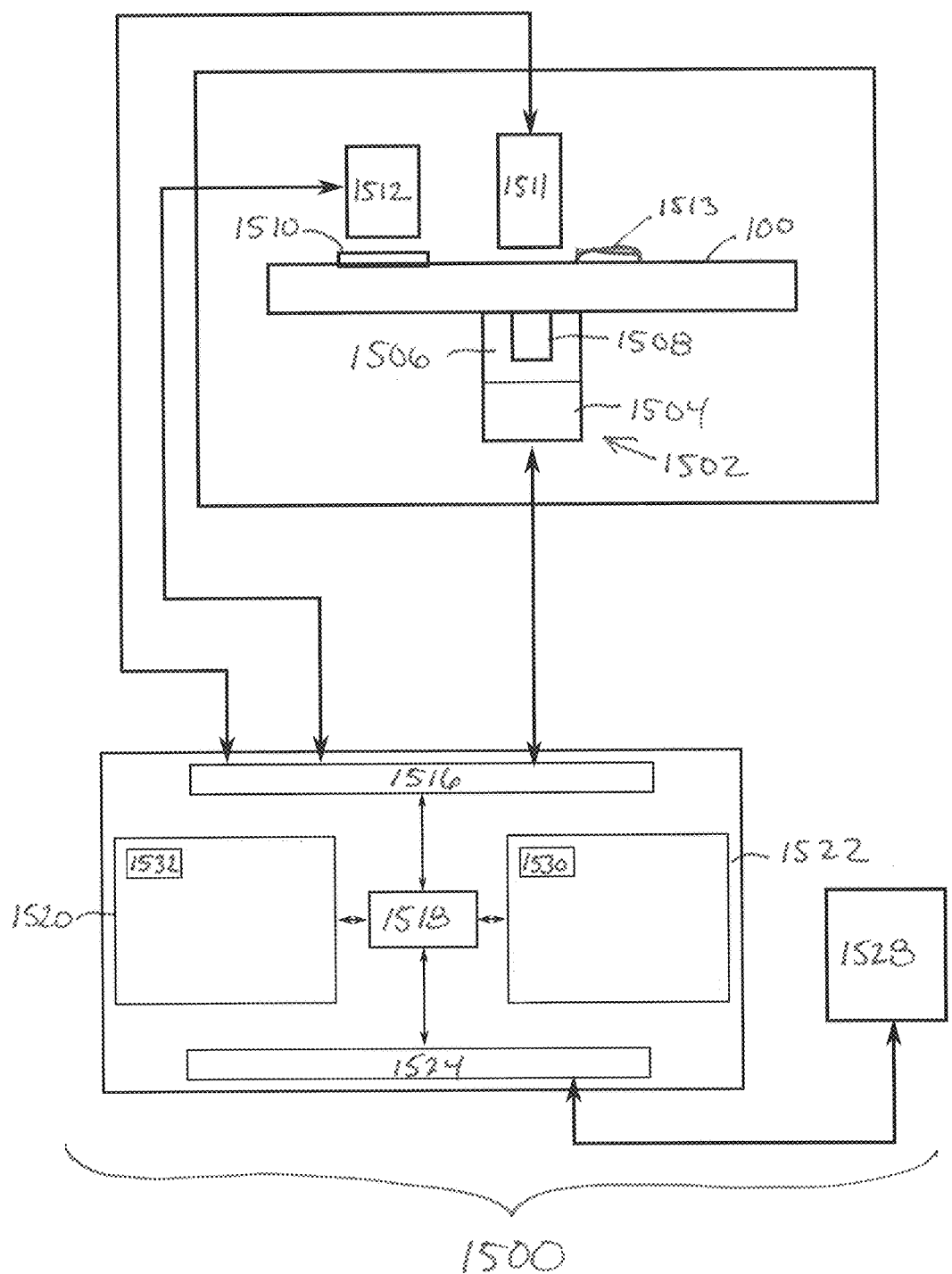
FIG. 15 illustrates an example of a blood collector.

FIG. 15 shows an example of a medical system 1500. The medical system 1500 is adapted for receiving a cartridge 100. There is a cartridge spinner 1502 which is operable for rotating the cartridge 100 about the rotational axis. The cartridge spinner 1502 has a motor 1504 attached to a gripper 1506 which attaches to a portion of the cartridge 1508. The cartridge 100 is shown further as having a measurement or transparent structure 1510. The cartridge 100 can be rotated such that the measurement structure 1510 goes in front of an optical measurement system 1512 which can perform for example an optical measurement of the quantity of the analyte. An actuator 1511 is also shown in this FIG. It can be used to open fluid reservoirs in the cartridge 100. There may also be additional actuators or mechanisms for actuating mechanical valves or valve elements on the cartridge if they are present. A blood collector 1513 is shown as being attached to the cartridge 100.

The actuator 1511, the cartridge spinner 1502, and the measurement system 1512 are shown as all being connected to a hardware interface 1516 of a controller 1514. The controller 1514 contains a processor 1518 in communication with the hardware interface 1516, electronic storage 1520, electronic memory 1522, and a network interface 1524. The electronic memory 1530 has machine executable instructions which enable the processor 1518 to control the operation and function of the medical system 1500. The electronic storage 1520 is shown as containing a measurement 1532 that was acquired when instructions 1530 were executed by the processor 1518. The network interface 1524 enables the processor 1518 to send the measurement 1532 via network connection 1526 to a laboratory information system 1528.

FIG. 16 shows a flowchart which illustrates a method of operating the medical system 1500 of FIG. 15. The flowchart in FIG. 16 illustrates the steps that are performed by the medical system 1500. They do not include steps that may be performed by a user or operator such as placing a blood sample into the capillary inlet or attaching the mounting surface to the receiving surface.

First in step 1600, the cartridge 100 is rotated about the rotational axis to transport the blood sample from the capillary structure to the cartridge inlet. Next in step 1602, the cartridge is rotated about the rotational axis to transport the blood sample from the cartridge inlet to the microfluidic structure. Next in step 1604, the rotation of the cartridge is controlled about the rotational axis to process the blood sample into the processed sample using the microfluidic structure. Next in step 1606, the rotation of the cartridge is controlled to transfer the processed sample to the measurement structure. Finally, in step 1608, the amount of analyte is measured using the measurement structure 1510 and the measurement system 1512.

LIST OF REFERENCE NUMERALS 100 cartridge
102 rotational axis
104 circular outer edge
106 flat outer edge
108 cartridge inlet
110 storage chamber
111 microfluidic structure
112 expansion chamber
112' expansion chamber
114 vent
116 failsafe indicators
118 blood separation chamber
120 overflow chamber
122 first valve structure
124 processing chamber
126 surface for reagent
128 second valve structure
130 measurement structure
132 absorbent structure
134 chromatographic membrane
136 fluid chamber
136' fluid chamber
138 fluid duct
138' fluid duct
140 metering structure
140' metering structure
142 manual fill location
144 aliquoting chamber
146 metering chamber
148 connecting duct
150 fluidic element
300 cartridge
302 fluid duct
400 blood collector
401 exposed surface
402 mounting surface
403 capillary inlet
404 capillary structure
406 curved portion
408 central region
410 outer channel (capillary stop)
412 spoke channel
414 sharp edge
416 rounded edge
418 flexible element
420 mounting surface
500 blood sample
502 visual indicator
600 cartridge
602 outer surface
800 blood collector
802 finger grip
803 lower surface
804 vent
806 first snap element
1100 touch capillary inlet to finger prick
1101 drop of blood
1102 visual inspection of blood sample
1104 snap blood collector onto cartridge
1106 cartridge
1106 cartridge with blood collector mounted
1200 blood collector
1202 first formed portion
1204 second foil portion
1206 elevated finger grip
1400 touch capillary inlet to finger prick
1402 visual inspection of blood sample
1404 snap blood collector onto cartridge
1406 cartridge
1500 medical system
1502 cartridge spinner
1504 motor
1506 gripper
1508 portion of cartridge
1510 measurement structure
1511 actuator
1512 optical measurement system
1513 blood collector
1514 controller
1516 hardware interface
1518 processor
1520 electronic storage
1522 electronic memory
1524 network interface
1526 network connection
1528 laboratory information system
1530 executable instructions
1532 measurement 1600 rotating the cartridge about the rotational axis to transport the blood sample from the capillary structure to the cartridge inlet 1602 rotating the cartridge about the rotational axis to transport the blood sample from the cartridge inlet into the microfluidic structure 1604 controlling the rotation of the cartridge about the rotational axis to process the blood sample into the processed sample using the microfluidic structure 1606 controlling the rotation of the cartridge to transfer the processed sample to the measurement structure 1608 measuring the amount of the analyte using the measurement structure and a measurement system

What is claimed:

1. A method of determining an amount of an analyte in a blood sample using a cartridge and a blood collector, wherein the cartridge is operable for being spun around a rotational axis,
the blood collector comprises a mounting surface, and a capillary structure for holding the blood sample,
the capillary structure comprises a curved portion, a capillary inlet for receiving the blood sample, a capillary channel, and a vent forming a capillary stop at an end of the capillary channel remote from the capillary inlet, wherein the capillary channel is transparent from the capillary inlet to the vent to form a visual indicator which indicates when the capillary structure is filled completely between the capillary inlet and the vent with a precise amount of the blood sample,
the cartridge comprises a receiving surface for attaching to the mounting surface, a cartridge inlet for receiving the blood sample from the blood collector, the blood collector being configured such that when the mounting surface is attached to the receiving surface the capillary inlet is in fluidic connection with the cartridge inlet, a microfluidic structure for processing the blood sample into a processed sample, the microfluidic structure being fluidically connected to the inlet, and a measurement structure for enabling measurement of the processed sample to determine the amount of the analyte in the blood sample, the method comprising:
placing the blood sample into the capillary inlet;
attaching the mounting surface to the receiving surface;
rotating the cartridge about the rotational axis to transport the blood sample from the capillary structure to the cartridge inlet;
rotating the cartridge about the rotational axis to transport the blood sample from the cartridge inlet into the microfluidic structure;
controlling the rotation of the cartridge about the rotational axis to process the blood sample into the processed sample using the microfluidic structure;
controlling the rotation of the cartridge to transfer the processed sample to the measurement structure;
controlling the rotation of the cartridge to position the measurement structure relative to a measuring system; and
measuring, via the measurement system, the amount of the analyte in the processed sample transferred to the measurement structure.

2. The method of claim 1, wherein the microfluidic structure comprises a blood separation chamber for separating blood plasma or serum from the blood sample, wherein the blood separation chamber is fluidically connected to the inlet, wherein the method further comprises:
rotating the cartridge about the rotational axis to transport the blood sample from the cartridge inlet into the blood separation chamber; and
controlling the rotation of the cartridge about the rotational axis to separate blood plasma from the blood sample by centrifugation, wherein the step of controlling the rotation of the cartridge about the rotational axis to process the blood sample into the processed sample using the microfluidic structure is performed such that the blood plasma is processed into the processed sample.

3. The method of claim 2, wherein the blood collector comprises a first snap element, wherein the cartridge comprises a second snap element configured for engaging the first snap element to lock the mounting surface to the receiving surface, and said method further comprises locking the mounting surface to the receiving surface via engaging the first and second snap elements.

4. The method of claim 2, further comprising attaching the blood collector to the cartridge via a flexible element of the cartridge that is configured for guiding the mounting surface to the receiving surface.

5. The method of claim 1, further comprising attaching the blood collector to the cartridge via a flexible element of the cartridge that is configured for guiding the mounting surface to the receiving surface.

6. A medical system comprising:
a cartridge with a receiving surface; and
a blood collector for storing a blood sample, wherein the blood collector comprises:
a mounting surface for attaching to the receiving surface of the cartridge; and
a capillary structure for holding the blood sample, wherein the capillary structure has a curved portion, a capillary inlet for receiving the blood sample, a capillary channel, and a vent forming a capillary stop at an end of the capillary channel remote from the capillary inlet, wherein the capillary channel is transparent from the capillary inlet to the vent to form a visual indicator which indicates when the capillary structure is filled completely between the capillary inlet and the vent with a precise amount of the blood sample; and
wherein the cartridge is operable for being spun around a rotational axis, and wherein the cartridge further comprises:
a cartridge inlet for receiving the blood sample from the blood collector, wherein the blood collector is configured such that when the mounting surface is attached to the receiving surface the capillary inlet is positioned at the cartridge inlet;
a microfluidic structure for processing the blood sample into a processed sample, wherein the microfluidic structure is fluidically connected to the inlet; and
a measurement structure for enabling measurement of the processed sample to determine an amount of an analyte in the processed sample.

7. The medical system of claim 6, wherein the microfluidic structure comprises a blood separation chamber for separating blood plasma from the blood sample, and wherein the blood separation chamber is fluidically connected to the inlet.

8. The medical system of claim 6, wherein the blood collector comprises a first snap element, and wherein the cartridge comprises a second snap element configured for engaging the first snap element to lock the mounting surface to the receiving surface.

9. The medical system of claim 8, wherein the capillary structure is formed from rigid plastic, wherein the capillary inlet is perpendicular to the capillary structure, wherein the capillary inlet extends beyond the mounting surface, and wherein the blood collector comprises a finger grip.

10. The medical system of claim 6, wherein the blood collector is attached to the cartridge via a flexible element of the cartridge that is configured for guiding the mounting surface to the receiving surface.

11. The medical system of claim 10, wherein the blood collector comprises an exposed surface, wherein the capillary structure is formed as open channels in the exposed surface, and wherein the capillary inlet is formed where the open channels meet the exposed surface.

12. The medical system of claim 6, wherein the blood collector comprises a foil portion, wherein the blood collector further comprises a formed portion, wherein the formed portion is plastic, wherein the capillary structure and the capillary inlet are formed in the formed portion, wherein the curved portion is parallel to a plane, wherein the foil portion is parallel to the plane, and wherein the foil portion forms a wall of the capillary structure.

13. The medical system of claim 6, wherein the medical system further comprises a cartridge spinner for controlling rotation of the cartridge about the rotational axis.

14. The medical system of claim 13, wherein the medical system comprises a memory for storing machine executable instructions and a processor for controlling the medical system, wherein execution of the machine executable instructions causes the processor to:
  rotate the cartridge about the rotational axis to transport the blood sample in the capillary structure to the cartridge inlet by controlling the cartridge spinner;
  rotate the cartridge about the rotational axis to transport the blood sample from the cartridge inlet into the microfluidic structure by controlling the cartridge spinner;
  control the rotation of the cartridge about the rotational axis to process the blood sample into the processed sample using the microfluidic structure by controlling the cartridge spinner;
  control the rotation of the cartridge to transfer the processed sample to the measurement structure by controlling the cartridge spinner; and
  measure the amount of the analyte in the processed sample transferred to the measurement structure via a measurement system external to the cartridge.

* * * * *